United States Patent [19]

Bowers et al.

[11] Patent Number: 5,368,706
[45] Date of Patent: Nov. 29, 1994

[54] AMPEROMETRIC DETECTION CELL

[75] Inventors: Mark L. Bowers, Arlington; David Buttaro, Woburn; W. Michael Krebs, Sudbury, all of Mass.

[73] Assignee: Esa, Inc., Bedford, Mass.

[21] Appl. No.: 180,830

[22] Filed: Jan. 12, 1993

Related U.S. Application Data

[63] Continuation of Ser. No. 827,534, Jan. 29, 1992, which is a continuation of Ser. No. 487,774, Mar. 2, 1990.

[51] Int. Cl.$^5$ .......................................... G01N 27/26
[52] U.S. Cl. ................................ 204/153.1; 204/291; 204/292; 204/400; 204/409; 204/412; 204/435
[58] Field of Search ................... 204/153.1, 291, 292, 204/400, 409, 412, 415, 435

[56] References Cited

U.S. PATENT DOCUMENTS

| | | | |
|---|---|---|---|
| 3,313,721 | 4/1967 | Teel | 204/290 F |
| 4,404,065 | 9/1983 | Matson | 204/153.1 |
| 4,426,621 | 1/1984 | Galwey et al. | 204/406 |
| 4,506,226 | 3/1985 | Luce et al. | 204/406 |
| 4,525,265 | 6/1985 | Abe | 204/415 |
| 4,536,274 | 8/1985 | Papadakis et al. | 204/415 |
| 4,547,280 | 10/1985 | Karasawa et al. | 204/415 |

*Primary Examiner*—T. Tung
*Attorney, Agent, or Firm*—Hayes, Soloway, Hennessey, Grossman & Hage

[57] ABSTRACT

An improved electrochemical detection cell comprising a palladium reference electrode.

3 Claims, 3 Drawing Sheets

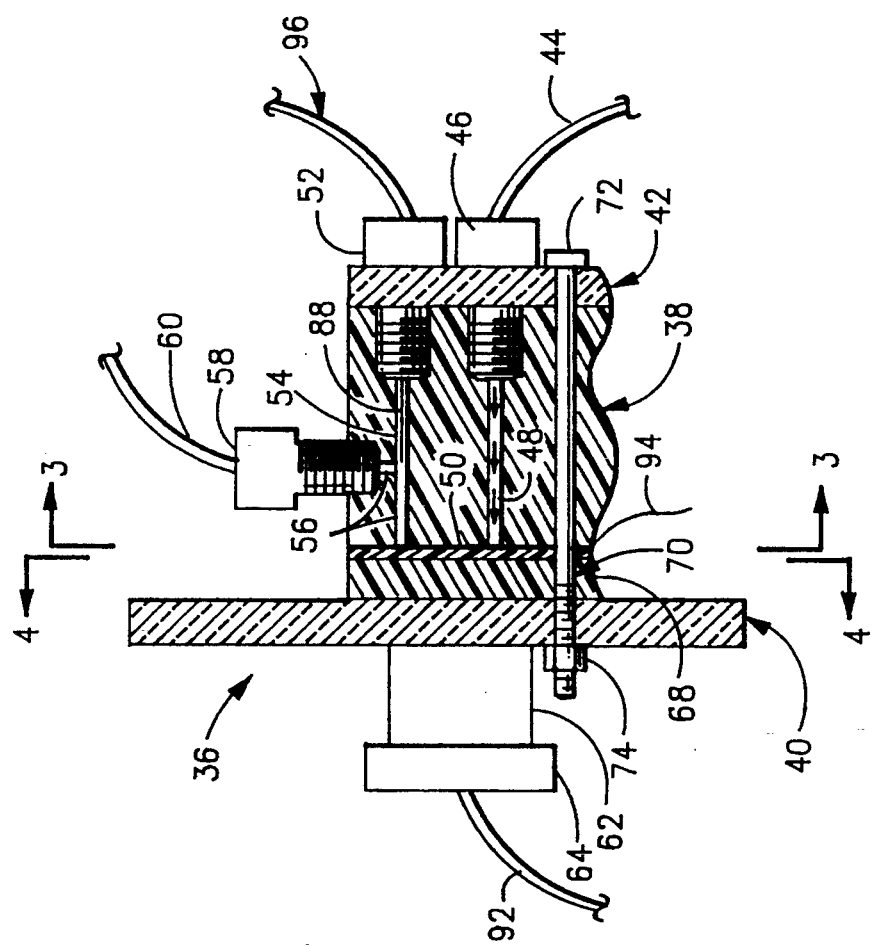
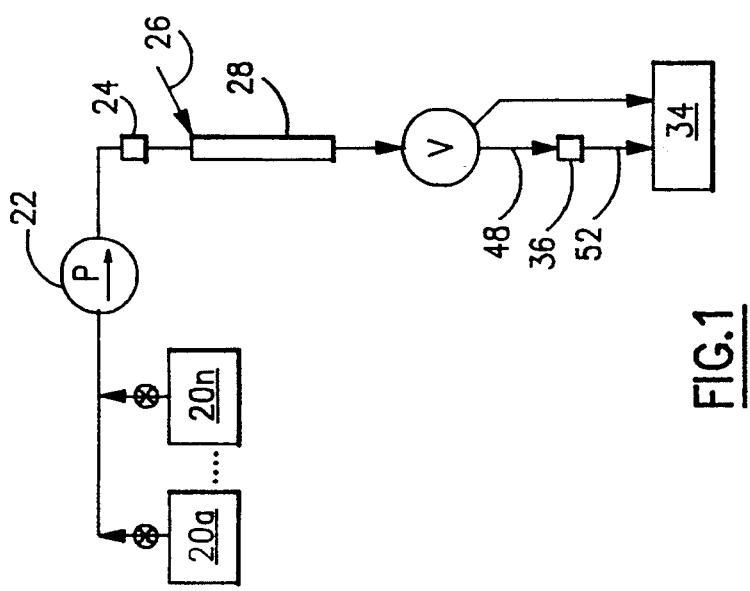
FIG.2
FIG.1

AMPEROMETRIC DETECTION CELL

This is a continuation of application Ser. No. 07/827,534, filed Jan. 29, 1992, now abandoned, which is in turn a continuation of application Ser. No. 07/487,774, filed Mar. 2, 1990, now abandoned.

The present invention relates to a new electrochemical detector device and more particularly, to a new amperometric detector cell for qualitatively and quantitatively testing electroactive materials in solution. The invention has particular utility in connection with liquid chromatography separations and detection of amino acids and carbohydrates and will be described in connection with such use, although other uses are contemplated.

INTRODUCTION

With the burgeoning interest in genetic engineering and biotechnology, the determination of amino acids for protein sequencing and analysis has become increasingly important.

Recent progress in amino acid determinations can be attributed, in part, to technological advances in liquid chromatography and chromatographic detectors. Separations of amino acids and their derivatives in liquid chromatography (LC) are readily achieved by using reversed-phase stationary phases and ion exchangers. For the separation of complex mixtures, gradient elution chromatography is essential.

In recent years, electrochemical detection with liquid chromatography has gained prominence as a sensitive and selective detection technique for electroactive groups. Amino acids and carbohydrates generally have not been considered to be electroactive. Direct anodic detection at constant applied potential (DC) can occur by catalytic mechanisms on certain transition-metal oxides, e.g. nickel and copper. However, catalytic DC detections on nobel-metal electrodes is accompanied by loss of electrode activity with rapid decay of analytical sensitivity.

Pulsed amperometric detection (PAD) and pulsed coulometric detection (PCD) following liquid chromatography have proven to be selective and sensitive techniques for the determination of alcohols, polyalcohols, carbohydrates, amino acids, aminoalkanols and many inorganic and organic sulfur-containing compounds. PAD uses a triple-step potential waveform to combine amperometric (PAD) detection followed by alternating anodic and cathodic polarizations to clean and reactivate the electrode surface whereas PCD uses three or more potential steps in a wave form to combine coulometric detection and eliminate the undesirable signal due to the electrode itself followed by the cleaning potential. In the detection of amino acids and carbohydrates, the waveform exploits the surface-catalyzed oxidation of the amine and alcohol functionalities activated by the formation of nobel metal surface oxides. Sensitivity in PCD is optimum at ca.pH>11, and postcolumn addition of base may be desired. However, the catalytic nature of PCD for amino acids limits the use of gradient elution chromatography because the base-line signal corresponds to the oxide formation process which is very sensitive to small changes in the mobile phase composition, especially the pH.

As reported by Welch et al in their article Comparison of Pulsed Coulometric Detection and Potential-Sweep Pulsed Coulometric Detection for Underivatized Amino Acids in Liquid Chromatography in *Analytical Chemistry*, 1989, 61, 555–559, a major limitation in the electrochemical detection with liquid chromatography is the inability to efficiently couple gradient chromatography with pulsed electrochemical detection. According to Welsh et al prior attempts to use a four-solvent gradient system LC/PCD for the separation of a 17-component hydrolyzate resulted in such a severe base-line shift, as predicted by the cyclic voltammograms, so as to make the chromatograms virtually useless. A major cause for the shifting of the surface oxide background is a change in pH. While a glass pH electrode reportedly results in a shift of the reference potential substantially in unison with the pH gradient, a comparison of three-gradient solvents by cyclic voltammetry using a pH reference electrode revealed that the anodic waves for oxide formation are nearly superimposed.

Another problem that is not generally recognized with amperometric detectors and especially amperometric detectors used in pulse detection is the large junction potentials and the large uncompensated current-resistance (IR) that is present with the generally used reference electrodes such as the silver/silver chloride and the saturated calomel electrode which are usually contained in glass tubes and separated from the flow stream by a porous glass or ceramic barrier. These typical reference electrode arrangements can lead to inadequate potential control of the working electrode and place larger demands on the compliance voltage of the potentiostat. These in turn can result in added noise and slower response of the EC detector.

We have found that the aforesaid and other problems of the prior art may be obviated by the use of a solid state palladium reference electrode. More particularly, in accordance with the present invention, an amperometric detection cell is provided comprising a three-electrode system consisting of a working electrode of conventional construction, for example, gold, platinum, glassy carbon or the like, a counter-electrode of conventional construction, and a solid state palladium reference electrode which is actually driven in response to changes in the test solution. Typically the reference electrode comprises at least one thin wire formed of palladium or palladium oxide, and the counter-electrode comprises a flat plate or foil formed of a metal such as platinum or gold. Alternatively, the counter-electrode may also be formed of palladium or palladium oxide.

For a further understanding of the nature and advantages of the present invention, reference should be had to the following detailed description taken in connection with the accompanying drawings, wherein like numbers denote like parts, and wherein:

FIG. 1 is a schematic view of one form of liquid chromatography apparatus incorporating an electrochemical detection apparatus in accordance with the present invention;

FIG. 2 is a side elevational view, in cross-section, of a preferred form of electrochemical detector made in accordance with the present invention;

Figure 4:
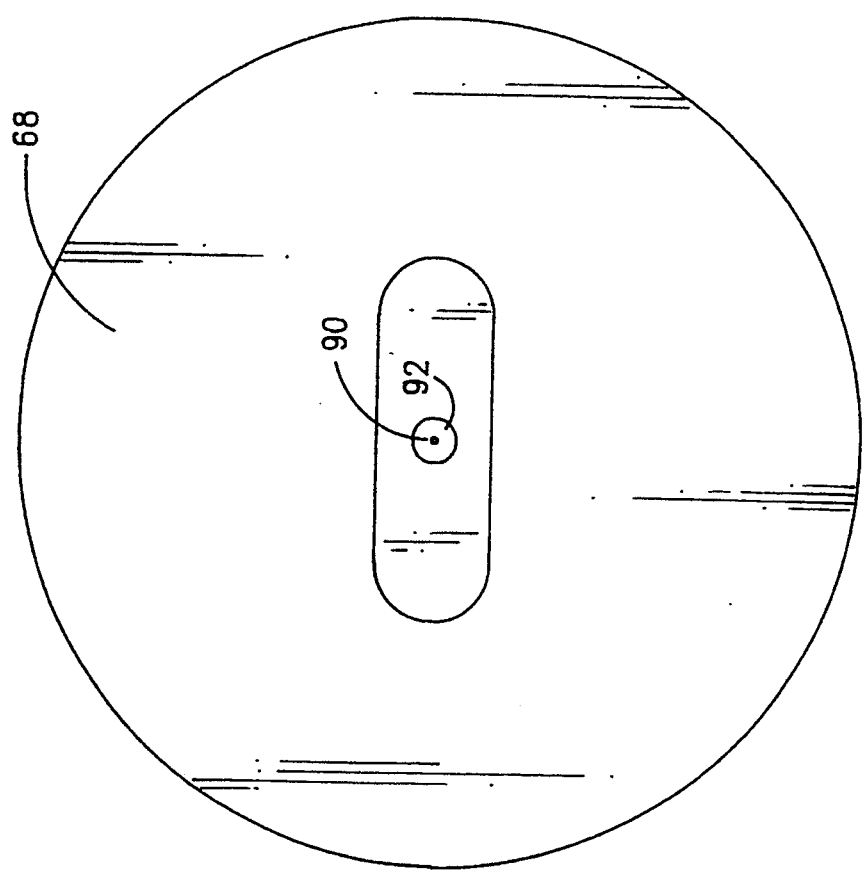
FIG. 4 is a cross-sectional view of the electrochemical detection cell of FIG. 2, taken along lines 4—4.

Referring to FIG. 1, there is illustrated a liquid chromatography apparatus and electrochemical detection apparatus in accordance with the present invention. The illustrated liquid chromatography apparatus includes mobile phase reservoirs 20a . . . 20n coupled through suitable valves a constant volume pump means 22 and an injection valve 24 and sample inlet 26 to the top of a liquid chromatography column indicated generally at 28. In practice, sample materials to be tested are introduced into the chromatography apparatus either by direct injection of microliter amounts of sample material into the chromatography column 28, e.g. through a syringe at sample inlet 26, or the sample material may be introduced into the chromatography column 28 as a dilute solution of sample material at injection valve 24. Thus, if desired, either injection valve 24 or sample inlet 26 may be omitted from the system. Chromatography column 28 is packed with selected ion exchange resins in bed or powder form. The selection of the mobile phase, and the selection and packing order of the ion exchange resins will depend on the particular separations desired and can readily be determined by one skilled in the art and thus will not be further described herein. The base of chromatography column 28 is coupled via an outlet 30 to a splitter valve 32 which divides the eluant from the chromatography column 28 between a sample collection vessel or waste container 34 and an electrochemical detection apparatus made in accordance with the present invention, and indicated generally at 36.

The illustrated chromatography apparatus (other than the electrochemical detection apparatus 36) is conventional and may be of the type described by P. H. Freeman and W. L. Zielinski, in U.S. Bureau of Standards Technological Note Number 589, Page 1, (July 1970 to June 1971). Moreover, it should also be noted that the electrochemical detection apparatus 36 of the present invention is not limited to use with the particular type of chromatography apparatus illustrated in FIG. 1, which is merely given as exemplary.

As mentioned supra, a problem with prior art amperometric detectors not employing pH reference electrodes, is the inability to compensate fully for pH gradient shifts resulting from the use of different mobile phases. The present invention overcomes the aforesaid and other disadvantages of prior art amperometric detectors by employing a solid state reference electrode formed of palladium or palladium oxide. The use of a solid state palladium reference electrode in a coulometric detection cell is described in U.S. Pat. No. 4,404,065 issued Sep. 13, 1983 to Wayne R. Matson, and assigned to the assignee of the present application. However, prior to the present invention, the advantages of employing a solid state palladium reference electrode in an amperometric cell were not recognized.

Figure 3:
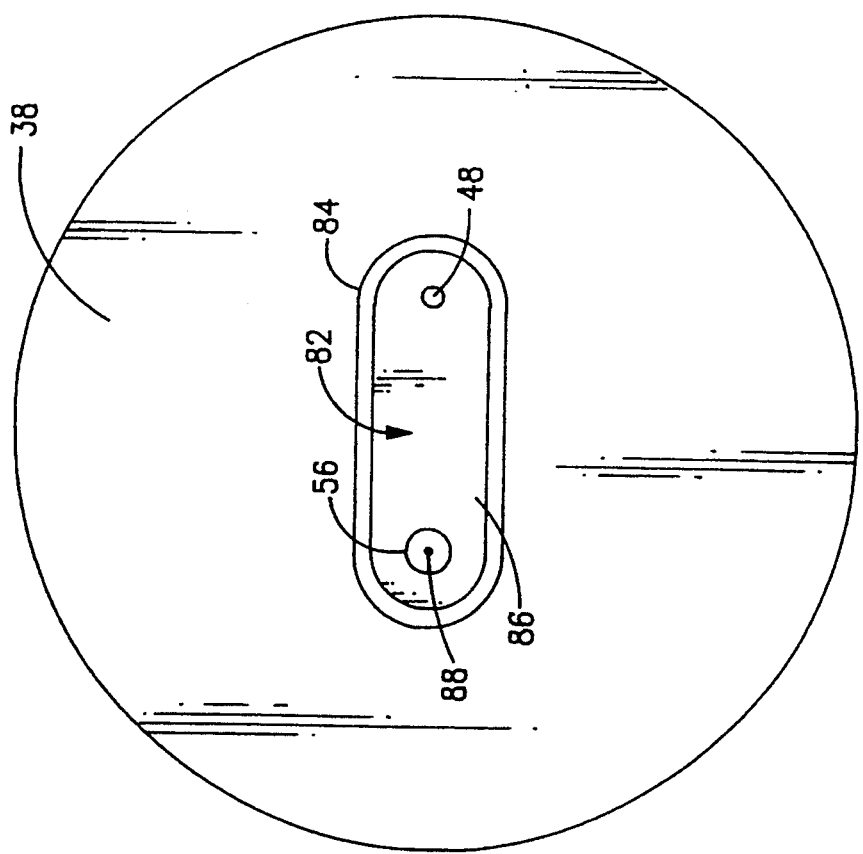
FIG. 3 is a cross-sectional view of an electrochemical detection cell of FIG. 2, taken along lines 3—3.

Referring to FIGS. 2 and 3, electrochemical detection apparatus 36 comprises an electrochemical detection cell comprising a cylindrical body 38 having a pair of end plates 40 and 42, respectively. Main cell body 38 and plates 40 and 42 comprise short, generally cylindrical plates formed of a rigid, liquid impervious, electrically-insulating, chemically inert material such as a synthetic polymeric material, e.g. a ceramic, an unplasticized polyvinyl chloride, a polytetrafluoroethylene fluorocarbon resin, or the like. An internally threaded screw mounting (not shown) is formed in plate 42 for connecting the outlet from chromatography column 28 via conduit 44 to an inlet 46. Inlet 46 communicates with a bore 48 formed in body 38 to the cell thin layer detection flow path indicated generally at 50. In a similar manner, the reference electrode assembly 52 is threadedly mounted through a internally threaded screw mounting (not shown) in plate 42 and communicates via a bore 54 with the thin layer flow path 50. Flow path 50 communicates through a bore 56 formed in the side wall of body 38 to a threaded fitting 58 fitted with an outlet conduit 60.

The test electrode assembly is mounted on plate 40, and comprises a cylindrical spacer member 62 and cap member 64 which are threaded together, and the assembly in turn is threaded into an internally threaded aperture (not shown) in plate 40. The test electrode is mounted in a bore (not shown) which extends through members 62 and 64 and through plate 40 to the interior of the electrode assembly. Completing the electrode chemical cell assembly is a rigid spacer member 68 and gasket 70 as will be described in detail hereinafter. Members 62 and 64 and spacer 68 all are formed of a rigid, liquid impervious electrically-insulating, chemically inert material. Gasket 70 preferably is formed of Teflon. A plurality of bolt holes 70 are formed through end plates 40, 42, spacer 68 and gasket 70 and provide entry for bolts, only one of which 72 is shown. Bolts 72 align the individual parts of the electrochemical detection cell and, when anchored with nuts 74, apply pressure to keep the electrochemical detection cell together.

Referring now to FIG. 3, a recess 82 is formed in body 38 to define the flow path 50, communicating with inlet 48 and outlet 56. A 0.25 millimeter thick palladium foil counter electrode 86 is positioned in the bottom of recess 82, and it is held in place by means of a Teflon gasket 84. A palladium wire reference electrode is threaded through bore 56.

Referring to FIG. 4, the testing electrode, which comprises a solid gold wire 90 is positioned with its end surface flush with the surface of spacer 68. A bushing member 92 formed of Teflon or the like, surrounds electrode 90, and maintains electrode 90 in position in the assembly.

Completing the electrode cell in accordance with the present invention are lead wires 92, 94 and 96 for connecting the testing electrode 90, counter electrode 86 and reference electrode 88 to controlled testing potentials, a working potentials (or ground), and reference potential.

Figure 5:
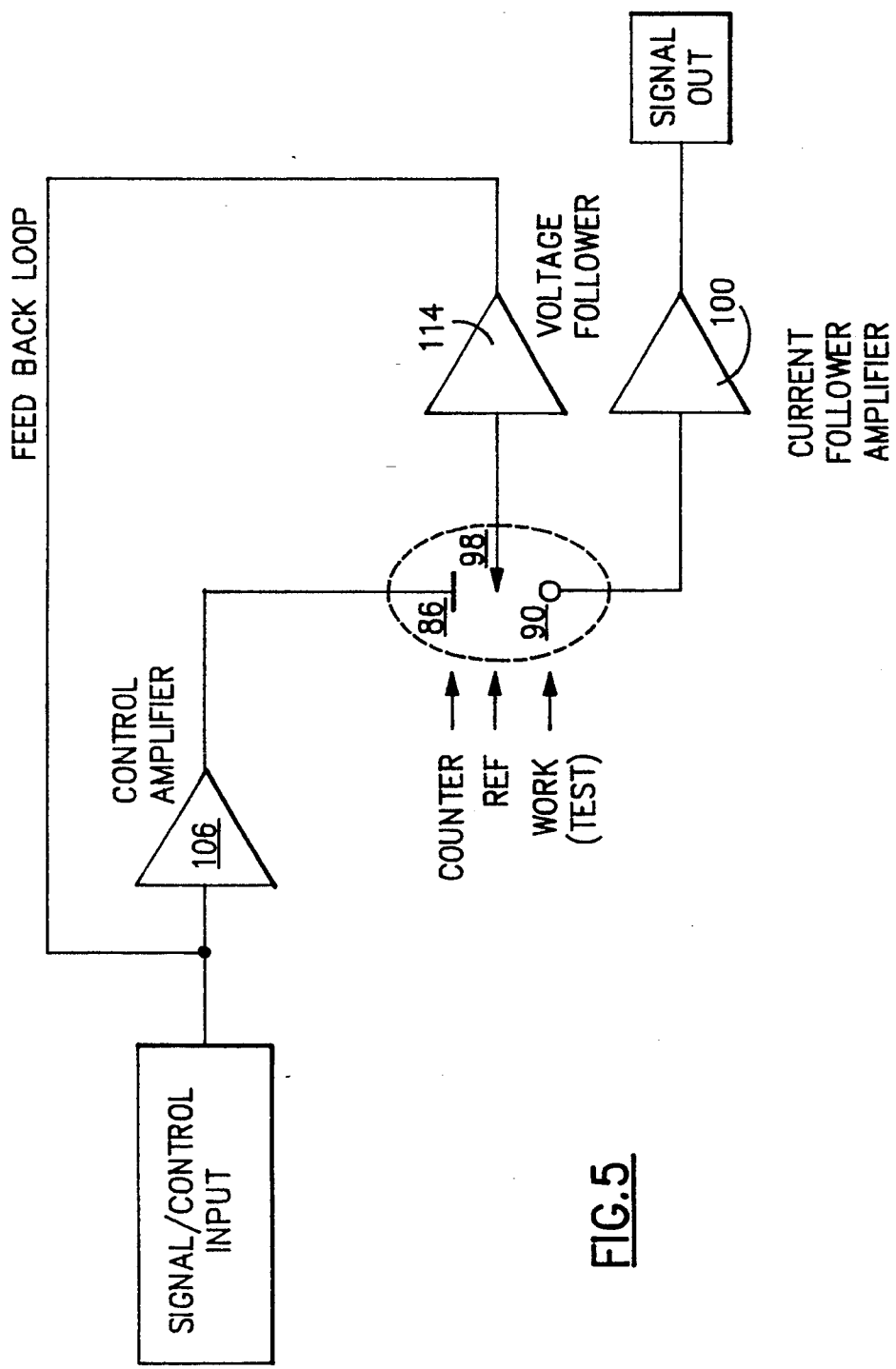
FIG. 5 is a diagrammatic sketch of a preferred form of reference electrode control circuit of the present invention.

As shown in FIG. 5, the electrical controls and circuits include a control amplifier 106 which controls the current that flows between the counter electrode 86 and the working electrode 90 by means of the potential set by the input and maintained between the reference electrode 88 and the working electrode 90 via the feedback arrangement between the reference electrode 88, the voltage follower 114, and the input to the control amplifier 106. The thermodynamic state of the reference electrode(s) will change in response to the changing pH of the mobile phase gradient and the circuit will automatically keep the applied potential between the reference and the working electrodes to that set by the input signal thus effectively responding to the pH gradient change of the mobile phase. This in turn keeps the desired catalytic potential of the working electrode at its optimal value throughout the gradient thus permitting compensation for the gradient elution changes and also avoids the maintenance problems and leakage problems typically associated with conventional glass electrodes.

As should be clear from the foregoing, the electrochemical detection apparatus of the present invention offers a number of advantages over prior art electrochemical detectors.

It is to be appreciated that the invention is not limited to application to liquid chromatography, but, rather the electrochemical detection apparatus may also be employed to monitor and/or measure the progress of a gas chromatographic separation process. In this regard, in some cases it may be possible to measure concentration or constitutional changes in the gases directly. In other cases it will be necessary to carry out the method in the presence of a liquid, preferably an electrolyte, e.g. by dissolving the eluant gas from the gas chromatography apparatus in an electrolyte and passing the electrolyte through the electrochemical detection cell.

Furthermore, the electrochemical detection apparatus is not limited to use with chromatography separations, but may also be advantageously employed for monitoring or directly measuring a variety of sample solutions, for example, of industrial, environmental, geophysical and biomedical interest. For example, the electrochemical detection apparatus of the present invention may be employed to provide on-line monitoring of a chemical process flow stream or a public water supply system, or for monitoring effluent from a sewage treatment facility.

Moreover, the electrochemical detection apparatus made in accordance with the instant invention is not limited to measuring only those compounds capable of undergoing electrochemical reactions, but also is capable of capacitive monitoring streaming solutions. For example, the measuring electrochemically nonreactive materials, a repetitive pulse of short duration, e.g. 10 to 20 $\mu$sec., may be fed to current amplifier 100 and a capacitive spike accumulated in a signal accumulator for a period of time, e.g. 100 to 500 $\mu$sec. prior to the calibration and recording. In this way any substance capable of changing the capacitance of the electrode double-layer can be seen at the signal output.

Still other features, modifications, advantages and objects will be obvious to one skilled in the art.

We claim:

1. In a method of electrochemically testing a sample solution by passing said solution through a thin layer detection flow path of an electrochemical flow cell, said flow cell comprising an amperometric flow cell having operatively disposed in said thin layer detection flow path a testing electrode, a counter electrode and at least one reference electrode, wherein said at least one reference electrode consists of a solid state palladium electrode, the improvement which comprises enhancing potential control of the testing electrode by sensing electrochemical changes in said sample solution through a voltage follower, and actively driving said reference electrode through a feed back loop in response to electrochemical changes in the sample solution, and said counter electrode comprises a palladium or palladium oxide foil defining one side of the thin layer detection flow path.

2. A method according to claim 1, wherein said reference electrode(s) comprises at least one thin wire formed of palladium.

3. A method according to claim 1 and including the steps of connecting said testing electrode to controlled testing potentials, connecting said counter electrode to a counter potential or ground, and connecting said reference electrode(s) to a reference potential through said voltage follower and feed back loop.

* * * * *